United States Patent
Day et al.

(10) Patent No.: US 10,827,757 B2
(45) Date of Patent: Nov. 10, 2020

(54) BIOCIDALLY ACTIVE POLYMER COMPOSITIONS

(71) Applicant: Lubrizol Advanced Materials, Inc., Cleveland, OH (US)

(72) Inventors: Roger W. Day, Solon, OH (US); Hua Zhang, Cottonwood Heights, UT (US); Richard Woofter, Medina, OH (US); Umit G. Makal, Stow, OH (US)

(*) Notice: Subject to any disclaimer, the term of this patent is extended or adjusted under 35 U.S.C. 154(b) by 0 days.

(21) Appl. No.: 15/767,771

(22) PCT Filed: Oct. 12, 2016

(86) PCT No.: PCT/US2016/056531
§ 371 (c)(1),
(2) Date: Apr. 12, 2018

(87) PCT Pub. No.: WO2017/066242
PCT Pub. Date: Apr. 20, 2017

(65) Prior Publication Data
US 2019/0191703 A1    Jun. 27, 2019

Related U.S. Application Data

(60) Provisional application No. 62/240,090, filed on Oct. 12, 2015.

(51) Int. Cl.
| | |
|---|---|
| *A01N 25/10* | (2006.01) |
| *A01N 33/12* | (2006.01) |
| *A01N 47/44* | (2006.01) |
| *A61L 2/00* | (2006.01) |
| *A61L 29/00* | (2006.01) |
| *A61L 31/00* | (2006.01) |
| *A61L 33/00* | (2006.01) |
| *C08K 5/00* | (2006.01) |
| *A01N 47/40* | (2006.01) |
| *A61L 27/34* | (2006.01) |
| *A61L 27/54* | (2006.01) |
| *A61L 29/08* | (2006.01) |
| *A61L 29/16* | (2006.01) |
| *A61L 31/10* | (2006.01) |
| *A61L 31/16* | (2006.01) |
| *A61L 15/22* | (2006.01) |
| *A61L 15/44* | (2006.01) |

(52) U.S. Cl.
CPC ............ *A01N 47/40* (2013.01); *A01N 25/10* (2013.01); *A01N 33/12* (2013.01); *A01N 47/44* (2013.01); *A61L 2/00* (2013.01); *A61L 15/225* (2013.01); *A61L 15/44* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *C08K 5/00* (2013.01); *A61L 2300/206* (2013.01); *A61L 2300/404* (2013.01)

(58) Field of Classification Search
None
See application file for complete search history.

(56) References Cited

U.S. PATENT DOCUMENTS

| | | | |
|---|---|---|---|
| 3,728,151 A | 4/1973 | Sherman et al. | |
| 3,995,085 A | 11/1976 | McCown | |
| 4,921,691 A | 5/1990 | Stockel | |
| 6,090,901 A | 7/2000 | Bowers et al. | |
| 6,207,777 B1 | 3/2001 | Shimada et al. | |
| 6,268,440 B1 | 7/2001 | Kudo et al. | |
| 6,287,707 B1 | 9/2001 | Luthra et al. | |
| 2003/0097120 A1 | 5/2003 | Santerre | |
| 2006/0217515 A1 | 9/2006 | Getman et al. | |
| 2006/0223962 A1 | 10/2006 | Getman et al. | |
| 2009/0211968 A1 | 8/2009 | Ho et al. | |
| 2010/0069946 A1 | 3/2010 | Cromack et al. | |
| 2011/0200655 A1 | 8/2011 | Black et al. | |
| 2011/0207841 A1 | 8/2011 | Kosar et al. | |
| 2011/0233810 A1 | 9/2011 | Neigel et al. | |
| 2012/0136087 A1 | 5/2012 | Parakka et al. | |
| 2012/0148774 A1 | 6/2012 | Mullick et al. | |
| 2013/0178125 A1 | 7/2013 | Jiang et al. | |
| 2013/0183262 A1 | 7/2013 | Wynne et al. | |

FOREIGN PATENT DOCUMENTS

| | | | | |
|---|---|---|---|---|
| EP | 0393511 A2 | 10/1990 | | |
| FR | 2686610 A1 | 7/1993 | | |
| GB | 2349644 A | 11/2000 | | |
| JP | 2001294810 A | 10/2001 | | |
| JP | 2014-231056 | * 12/2014 | ............ | C08F 293/00 |
| WO | 99/32157 A2 | 7/1999 | | |
| WO | 2009/148880 A2 | 12/2009 | | |
| WO | 2015/042020 A1 | 3/2015 | | |
| WO | 2016/172460 A1 | 10/2016 | | |
| WO | WO-2016172460 A1 | * 10/2016 | ............ | A61L 27/34 |

* cited by examiner

*Primary Examiner* — Brian Gulledge
(74) *Attorney, Agent, or Firm* — Thoburn Dunlap; Teresan Gilbert

(57) ABSTRACT

A biocidally active polymer composition formed from an oligomeric or polymeric additive and a thermoplastic polyurethane polymer is disclosed. The biocidally active polymer may further include a non-fouling and/or non-thrombogenic polymer. The biocidally active polymer provides biocidally active properties, and may also provide non-fouling and/or non-thrombogenic properties. The composition is particularly useful in articles and materials for medical applications.

50 Claims, No Drawings

BIOCIDALLY ACTIVE POLYMER COMPOSITIONS

CROSS REFERENCE TO RELATED APPLICATION

This application claims priority from PCT Application Serial No. PCT/US2016/056531 filed on Oct. 12, 2016, which claims the benefit of U.S. Provisional Application No. 62/240,090 filed on Oct. 12, 2015, both of which are incorporated in their entirety by reference herein.

FIELD OF THE INVENTION

There is provided an anti-microbial oligomeric or polymeric additive, as well as an anti-microbial polymer composition which includes the oligomeric or polymeric additive and a base polymer. The additive can include bloom-promoting, adherence-promoting, and biocidally active monomers and/or groups. The additive may further include a non-fouling and/or non-thrombogenic monomer and/or groups. The polymer composition may optionally contain non-fouling additives in addition to the antimicrobial additives disclosed in this application. The polymer composition including the additive(s) may find use in medical devices where anti-microbial, non-fouling and/or non-thrombogenic characteristics are of particular importance.

BACKGROUND

Healthcare associated infections ("HAIs") are one of the most common adverse events in healthcare delivery, affecting millions of patients each year. Owing to the associated costs, both monetarily and humanitarily, significant effort has been focused on reducing the incidence and severity of HAIs. However, even with substantial effort to ensure good hygiene and sterility practices in medical procedures, the rate of HAIs remains unacceptably high.

One approach to decreasing the incidence of HAIs, and particularly biomaterial associated infections, has been the development of biomaterials with antimicrobial properties and biofilm resistant surfaces. Various approaches have been taken to impart antimicrobial properties to biomaterials including absorption of antimicrobial or antiseptic agents into biomaterials, adsorbing or grafting antimicrobial agents onto the surface of biomaterials, and coating of biomaterials with antimicrobial coatings. These approaches, while effective, are typically costly, involve complex secondary processing steps, and often offer antimicrobial protection which is limited in duration. It is also well known that coatings used on biomaterials which contact the bloodstream often can flake off from the surface of the biomaterial and result in emboli downstream of the biomaterial, resulting in adverse medical outcomes. As such, there is significant interest in the medical device industry for biomaterials which have inherent antimicrobial properties and which do not require coatings and from which antimicrobial compounds do not leach over time. It is also advantageous if such biomaterials can be processed by any of a variety of methods, including, but not limited to extrusion, injection molding, compression molding, and electrospinning in addition to coating.

Polymers in general and particularly thermoplastic polyurethanes (TPUs) are widely used as biomaterials owing to their excellent physical and mechanical properties. Surface modification of polymers for biomedical applications has previously been accomplished by a variety of means, including coating the surface via dip coating or spray coating, or plasma polymerization of appropriate materials onto the polymer surface. Further, the addition of additives, such as fluorocarbons, which are non-compatible with the polymer and spontaneously migrate to the polymer surface, have been used to modify the polymer surface. Fluorocarbon surfaces, however, do not prevent fouling by proteins and do not provide biocidal or other active antimicrobial properties to the biomaterial.

It would be desirable, then, to provide a polymer composition that is biocidally active and may additionally exhibit non-fouling and/or non-thrombogenic characteristic.

SUMMARY

The disclosed technology provides an anti-microbial polymer composition which includes a) an oligomeric or polymeric additive formed from (i) a biocidally active monomer or group; (ii) a bloom-promoting silicone and/or fluorocarbon monomer or group; (iii) optionally, an adhesion-promoting monomer or group; and b) a base polymer.

The disclosed technology further provides an anti-microbial polymer composition further including a non-fouling monomer.

The disclosed technology further provides an anti-microbial polymer composition in which the oligomeric or polymeric additive is derived from (i) a bloom-promoting silicone or fluorocarbon-based acrylate, methacrylate, acrylamide or vinyl monomer; (ii) a biocidally active acrylate, methacrylate, acrylamide or vinyl monomer; and (iii) optionally, an adhesion-promoting monomer or group.

The disclosed technology further provides an anti-microbial polymer composition in which the oligomeric or polymeric additive is derived from (i) a silicone or fluorocarbon-based monomer containing an active hydrogen compound; (ii) a biocidally active monomer containing an active hydrogen; (iii) optionally, an adhesion-promoting monomer or group containing an active hydrogen; and (iv) a polyisocyanate.

The disclosed technology further provides an article containing the anti-microbial polymer composition. The article may be, in one embodiment, a medical device.

The disclosed technology further provides a method of making a biocidally active polymer composition by (a) free-radically polymerizing appropriate monomers to form the oligomeric or polymeric additive; and (b) incorporating the additive into the base polymer.

The disclosed technology further provides a method of making the biocidally active polymer composition by (a) reacting the polyisocyanate and active-hydrogen monomers to form the oligomeric or polymeric additive; and (b) incorporating the additive into the base polymer.

The disclosed technology further provides that incorporating the polymeric or oligomeric additive into the base polymer can include melt mixing of the additive into the base polymer or addition of the additive during synthesis of the base polymer.

The disclosed technology further provides that incorporating of the polymeric additive into the base polymer can include dissolving the additive and base polymer in a common solvent and casting, coagulating, or electrospinning the solvent mixture containing the additive and the base polymer.

The disclosed technology further provides an antimicrobial additive composition including an oligomeric or polymeric additive derived from (i) a bloom-promoting silicone or fluorocarbon-based acrylate, methacrylate, acrylamide or vinyl monomer; (ii) a biocidally active acrylate, methacrylate, acrylamide or vinyl monomer; and (iii) optionally, an adhesion-promoting monomer or group.

The disclosed technology further provides an antimicrobial additive composition including an oligomeric or polymeric additive derived from (i) a silicone or fluorocarbon-based monomer containing an active hydrogen group; (ii) a biocidally active monomer containing an active hydrogen group; (iii) optionally, an adhesion-promoting monomer or group containing an active hydrogen group; and (iv) a polyisocyanate.

The disclosed technology further provides antimicrobial monomers which can be prepared by relatively simple means and which can be readily incorporated into the antimicrobial additives by the methods described herein.

DETAILED DESCRIPTION

Various preferred features and embodiments will be described below by way of non-limiting illustration.

The disclosed technology provides a biocidally active polymer composition that includes an oligomeric or polymeric additive formed from a silicone or fluorocarbon (bloom-promoting) monomer, an adhesion-promoting monomer or group, and a biocidally active monomer. In one embodiment, the polymer composition includes a) an oligomeric or polymeric additive formed from one or more of i) a silicone or fluorocarbon monomer, or combinations thereof; ii) an adhesion promoting monomer or group; iii) a biocidally active monomer; and b) a base polymer. By biocidally active it is meant that the polymer has antimicrobial, biocidal, biostatic, antibacterial, fungicidal, virucidal, antifungal, and/or antiviral properties. In some embodiments, the oligomeric or polymeric additive further includes ii) a phosphorylcholine, a carboxybetaine, a sulfobetaine or a polyalkylene glycol monomer.

The Oligomeric or Polymeric Additive

The antimicrobial composition as disclosed herein includes an oligomeric or polymeric additive. In one embodiment, the additive includes dimers, trimers, or tetramers. In one embodiment, the additive includes a block, a graft or a branched polymer or copolymer. In one embodiment, the oligomeric or polymeric additive has a molecular weight (Mn) of from 1,000 to 50,000 daltons. In one embodiment, the additive has a molecular weight of from 2,000 to 15,000 daltons.

The oligomeric or polymeric additive may be present in the anti-microbial polymer composition, in some embodiments, in an amount from about 0.1 wt % to about 20 wt % of the total polymer composition, or from about 0.1 to about 10 wt %, and in one embodiment from about 0.5 wt % to about 5 wt %, or at least 0.2 wt %.

The Bloom-Promoting Silicone or Fluorocarbon Monomer

The oligomeric or polymeric additive of the surface-modified polymer composition disclosed herein can include a bloom-promoting monomer or group. The bloom-promoting monomer can include a silicone or fluorocarbon monomer, or combinations thereof.

In one embodiment, the silicone monomer includes a functionalized polysiloxane. The functionalized polysiloxane can be mono- or multi-functionalized. Suitable examples of functionalized polysiloxane include mono- or multi-functionalized acrylate, methacrylate, vinyl or allyl functionalized polysiloxanes, such as mono vinyl terminated polydimethylsiloxanes; mono methacryloxypropyl terminated polydimethylsiloxanes, vinyl terminated trifluoropropylmethylsiloxane; and monoallyl-mono trimethylsiloxy terminated polyethylene oxide. The polysiloxanes may generally have a molecular weight (Mn) of from 100 to about 100,000. The functional groups may be terminal, internal, or terminal and internal.

The functional polysiloxane may be represented by the following formula:

A-B-C wherein A is a polymerizable group selected from vinyl, acrylate, or methacrylate or an active hydrogen group selected from an alcohol, an amine or a thiol; B is an optional linking group, and C is a polysiloxane group.

Functionalized polysiloxanes which are useful in the additives of the invention are available commercially from a variety of sources. For example, terminally functionalized polysiloxanes are available from Evonik Industries under the Tegomer® range of products, including Tegomer® C-Si 2342 (Dicarboxyalkylpolydimethylsiloxane), Tegomer E-Si 2330 (Diepoxyalkylpolydimethylsiloxane), Tegomer®H-Si 2315 (Dihydroxyalkylpolydimethylsiloxane), and Tegomer® V-Si (Diacryloxypolydimethylsiloxane). Gelest Inc. also has various functional polysiloxane such as MCR-C12,18,22 series (MonoCarbinol Terminated polyDimethylsiloxane), MCR-C61,62 (MonoDiCarbinol Terminated PolyDimethylsiloxane), PDV series (Vinyl Terminated Diphenylsiloxane-Dimethylsiloxane Copolymers) FMV (Vinyl Terminated TrifluoropropylMethylsiloxane-Dimethylsiloxane Copolymer), CMS ((Carbinol functional)Methylsiloxane-Dimethylsiloxane Copolymers).

In some embodiments, the oligomeric or polymeric additive can include a fluorocarbon monomer. The fluorocarbon monomer may be represented by the following formula:

D-E-F wherein D is a polymerizable group selected from acrylate, methacrylate or vinyl or an active hydrogen group selected from an alcohol, an amine or a thiol, E is an optional linking group; and F is fluorocarbon group which can be perfluorinated or partially fluorinated.

Suitable fluorocarbon monomers include, but are not limited to 1,1,1,3,3,3-hexafluoroisopropyl acrylate, 1,1,1,3,3-hexafluoroisopropyl methacrylate, 2,2,3,4,4,4-hexafluorobutyl methacrylate, 2,2,3,3-tetrafluoropropyl methacrylate, 2,2,2-trifluoroethyl methacrylate, 2,2,3,3,4,4,4-heptafluorobutyl acrylate, 2,2,3,3,4,4,4-Heptafluorobutyl methacrylate, 2,2,3,3,3-Pentafluoropropyl acrylate, 2,2,3,3,4,4,5,5-Octafluoropentyl methacrylate, 2,2,3,3,3-Pentafluoropropyl methacrylate, 3,3,4,4,5,5,6,6,7,7,8,8,8-Tridecafluorooctyl methacrylate, 3,3,4,4,5,5,6,6,7,7,8,8,9,9,10,10,10-Heptadecafluorodecyl methacrylate, 3,3,4,4,5,5,6,6,7,7,8,8,8-Tridecafluorooctyl acrylate, 3,3,4,4,5,5,6,6,7,7,8,8,9,9,10,10,11,11,12,12,12-Heneicosafluorododecyl acrylate, 2,2,3,3,4,4,5,5-Octafluoropentyl acrylate, 2,2,3,3,4,4,5,5,6,6,7,7-Dodecafluoroheptyl acrylate 95%, 2,2,3,4,4,4-Hexafluorobutyl acrylate, 1H,1H,2H,2H-Perfluorodecyl acrylate, 2-[(1',1',1'-Trifluoro-2'-(trifluoromethyl)-2'-hydroxy)propyl]-3-norbornyl methacrylate, 1,1,1-Trifluoro-2-(trifluoromethyl)-2-hydroxy-4-methyl-5-pentyl methacrylate, 2-(Perfluorohexyl)ethyl methacrylate, 3,3,4,4,5,5,6,6,7,7,8,8,8-tridecafluoro-1-octanol, 4-Vinylbenzyl Hexafluoroisopropyl Ether, 4-Vinylbenzyl Perfluorooctanoate, 4-Vinylbenzyl Trifluoroacetate, Allyl Heptafluorobutyrate, Allyl Perfluoroheptanoate, Allyl Perfluorononanoate, Allyl Perfluorooctanoate, Allyl Tetrafluoroethyl Ether, Allyl Trifluoroacetate, Allylpentafluorobenzene, and perfluorinated polyether molecules with hydrogenated end groups containing hydroxyl reactive groups such as those sold under the tradename Fluorolink® by Solvay.

The silicone or fluorocarbon monomer can be present, in one embodiment, in an amount from about 5 wt % to about 60 wt % of the total monomer composition of the additive.

The Adhesion Promoting Monomer

In some embodiments, the oligomeric or polymeric additive includes an adhesion-promoting monomer or group. The adhesion-promoting monomer can include an alkyl substituted monomer. In one embodiment, the alkyl substituted monomer includes a methacrylate, an acrylate, an acrylamide or a vinyl monomer, or combinations thereof. Suitable monomers include, but are not limited to, substituted acrylates and methacrylates such as methyl methacrylate, ethyl acrylate, butyl acrylate, butyl methacrylate, 2-ethylhexylmethacrylate, mono and other similar monomers which will be readily obvious to those skilled in the art. The monomer may be chosen such that, when included in the additive, it will increase the affinity of the additive to the base polymer. In some embodiments, the alkyl substituted monomer will be present in the additive in an amount of from about 10 mole % to about 70 mole % of the total monomer composition of the additive.

In some embodiments, the alkyl substituted monomer can include hydroxyalkyl acrylates, acrylates with primary, secondary, or tertiary amino groups, and reactive or crosslinkable acrylate, such as acrylates containing silyl groups, double bonds, or other reactive functional groups; acrylamides, including substituted acrylamides as described above for acrylates; vinyl compounds; multifunctional molecules, such as di-, tri-, and tetraisocyanates, di-, tri-, and tetraols, di-, tri-, and tetraamines, and di-, tri-, and tetrathiocyanates; cyclic monomers, such as lactones and lactams; and combinations thereof; Alkyl methacrylates or other hydrophobic methacrylates, such as ethyl methacrylate, butyl methacrylate, hexyl methacrylate, 2-ethylhexyl methacrylate, methyl methacrylate, lauryl methacrylate, isobutyl methacrylate, isodecyl methacrylate, phenyl methacrylate, decyl methacrylate, 3,3,5-trimethylcyclohexyl methacrylate, benzyl methacrylate, cyclohexyl methacrylate, stearyl methacrylate, tert-butyl methacrylate, tridecyl methacrylate, and 2-naphthyl methacrylate; Reactive or crosslinkable methacrylates, such as 2-(trimethylsilyloxy)-ethylmethacrylate, 3-(trichlorosilyl)propyl methacrylate, 3-(trimethoxysilyl)-propyl methacrylate, 3-[tris(trimethylsiloxy)silyl]propyl methacrylate, trimethylsilyl methacrylate, ally methacrylate, vinyl methacrylate, 3-(acryloyloxy)-2-hydroxypropyl methacrylate, 3-(diethoxymethylsilyl)propyl methacrylate, 3-(dimethylchlorosilyl)propyl methacrylate, isocyanates, such as 2-isocyanatoethyl methacrylate, glycidyl methacrylate, 2-hydroxyethyl methacrylate, 3-chloro-2-hydroxypropyl methacrylate, Hydroxybutyl methacrylate, glycol methacrylate, hydroxypropyl methacrylate, and 2-hydroxypropyl 2-(methacryloyloxy)ethyl phthalate.

The amount of the various monomers used to make the additives of the invention are typically in the range of 10-60 mole percent of the total additive composition. The amount of each particular monomer which is useful in the invention will depend on which specific monomer from each class of monomers is used and the base polymer into which the additive is being blended. For example, for a PTMEG based aromatic TPU, additives which contain from about 10 to about 30 mole percent of a fluorocarbon methacrylates, from about 10 to about 70 mole percent of polyethylene glycol methacrylate and from about 10 to about 80 mole percent of methyl methacrylate has been shown to be effective to impart non-fouling and/or non-thrombogenic surfaces to the TPU base polymer with which it is blended.

In some embodiments, for example, in the case of polymeric or oligomeric additives based on urethane chemistry, no additional adhesion-promoting monomers or groups are required, particularly when the base polymer is a polyurethane. While not wishing to be bound by any particular theory, it is believed that the urethane linkage in some formulations is sufficient to provide adhesion between the additive and the base polymer such that no additional monomers or groups are required to provide sufficient adhesion such that no leaching of the additive will occur when the polymer composition is exposed to various environments under typical use conditions.

The Biocidally Active Monomer

The oligomeric or polymeric additive of the surface-modified polymer composition disclosed herein includes a biocidally active monomer. In one embodiment, the biocidally active monomer includes an acrylate, a methacrylate, a norbonene, a vinyl, or an ally monomer bearing one or more alkyl or aryl quaternized ammonium, sulfonium or phosphonium groups, or combinations thereof. Suitable monomers may be represented by the following formula:

GHI where G is a group which can be further polymerized; and I is an antimicrobial functional group selected from one or more of ammonium, phosphonium, sulfonium, guanidinium or biguanidinium groups, and H is an optional linking group. In some embodiments, such monomers include, but are not limited to, n-hexyl dimethylaminoethoxyl methacrylate, N-alkyl vinyl pyridium, p-Vinylbenzyl tetramethylenesulfonium tetrafluoroborate, and other similar monomers which will be readily obvious to those skilled in the art. The monomer may be chosen such that, when included in the additive, it will kill and/or inhibit the growth of microbial organisms. In some embodiments, the biocidal monomer will be present in the additive in an amount of from about 0.5 wt % to about 50 wt % of the total monomer composition of the additive. In some embodiment, the biocidal monomer will be present in the additive in an amount from about 0.5 wt % to about 30 wt %, and in some embodiments in an amount of at least 10 wt %, or 20 wt %.

Alternatively, the methacrylate, acrylate or other biocidally active monomer may contain guanidinium or biguanidinium groups. For example, guanidinopropyl methacrylate (Arjen M. Funhoff, Cornelus F. van Nostrum, Martin C. Lok, Marjan M. Fretz, Daan J. A. Crommelin, and Wim E. Hennink, Bioconjugate Chem., 2004, 15, 1212-1220) can be used as the biocidally active monomer, in some embodiments. In other embodiments, the biocidally active monomer may be PHMB methacrylate, or other similar guanidine or biguanidine methacrylates or acrylates. The synthesis of PHMB methacrylate is described in U.S. Pat. No. 7,771,743. In other embodiments, the biocidally active monomer includes an acrylate or methacrylate ester prepared by reaction of p-chlorophenylguanidino ethanol. P-chlorophenylguanidnio ethanol can be readily prepared from p-chlorophenyldicyanamide and ethanol hydrochloride by standard synthetic methods known by those skilled in the art (see examples). Other guanidine or biguanidine acrylates, methacrylates or vinyl monomers which are readily obvious to those skilled in the art or which can readily be envisioned can also be used as the biocidally active monomer. Alternately, in some embodiments the biocidal monomer can contain active hydrogen groups which can react with isocyanates to give antimicrobial additives based on urethane chemistry. Examples of such monomers can readily be envisioned by those skilled in the art and can readily be prepared by well-known synthetic procedures. Examples of such monomers are 1,6-bis-hydroxyethylbiguanidino hexane and p-chlorophenylguanidino ethanol which can be prepared according to the procedure disclosed in the examples.

The Non-Fouling and/or Non-Thrombogenic Monomer

In some embodiments, the polymeric or oligomeric additive of the antimicrobial composition can further include a non-fouling monomer. The non-fouling monomer can include a zwitterionic monomer or a polyalkylene glycol monomer. In one embodiment, the additive of the composition as disclosed herein includes a zwitterionic monomer or a polyalkylene glycol monomer. The zwitterionic monomer can include one or more of a phosphorylcholine, a carboxybetaine or a sulfobetaine monomer, derivatives thereof, or combinations thereof. Zwitterions are molecules that carry formal positive and negative charges on non-adjacent atoms within the same molecule. Both natural and synthetic polymers, containing zwitterion functionality, have been shown to resist protein adhesion. In one embodiment, the zwitterionic monomer includes a phosphorylcholine moiety, a sulfobetaine moiety, a carboxybetaine moiety, derivatives thereof, or combinations thereof. In one embodiment, the zwitterionic monomer includes 2-hydroxyethyl methacrylate phosphorylcholine.

The sulfobetaine monomer can be selected from one or more of sulfobetaine acrylates, sulfobetaine acrylamides, sulfobetaine vinyl compounds, sulfobetaine epoxides, and mixtures thereof. In one embodiment, the monomer is a methacrylate containing the sulfobetaine group.

The carboxybetaine monomer can include carboxybetaine acrylates, carboxybetaine acrylamides, carboxybetaine vinyl compounds, carboxybetaine epoxides, and mixtures thereof. In one embodiment, the monomer is carboxybetaine methacrylate.

In some embodiments, the zwitterionic monomers incorporated into the oligomeric or polymeric additives are present in an amount from 10-40 mole percent of the total monomer composition of the additive.

In one embodiment, the oligomeric or polymeric additive can further include a polyalkylene glycol monomer. In a further embodiment, the oligomeric or polymeric additive can alternatively include a polyalkylene glycol monomer, where the polyalkylene glycol monomer is utilized in place of or in addition to the zwitterionic monomer. Suitable polyalkylene glycol monomers include, but are not limited to acrylate, methacrylate esters of monomethyl polyethylene glycol polyols having a total of from 2 to 100 carbon atoms. Useful commercial polyalkylene glycol monomers include poly(ethylene glycol) comprising ethylene oxide reacted with ethylene glycol or other alcohol, such as poly(ethylene glycol) methyl ether methacrylate/acrylate with various molecular weights, glycol butyl ether methacrylate/acrylate with various molecular weights, poly(ethylene glycol) methacrylate/acrylate with various molecular weights. In some embodiments, the polyalkylene glycol monomer contains an active hydrogen reactive group, such as a hydroxyl, amine, or thiol. In one embodiment, the additive is formed using condensation polymerization, in which, for example, a diisocyanate is allowed to react with polyalkylene glycol monomers with active hydrogen groups. Tegomer® D3403 (a diol monomer available from Evonik with a pendant PEG group—similar monomers are available from Perstorp under the Ymer trade name) is one particularly useful monomer for the preparation of additives of this type. In some embodiments, the polyalkylene glycol monomer can be present in an amount from about 10 mole % to about 50 mole % of the total monomer composition of the additive.

Synthesis of Oligomeric or Polymeric Additives

The oligomeric or polymeric additive as disclosed herein may be formed via addition polymerization (radical, cationic and ionic) or condensation polymerization. In one embodiment, the additive is formed using addition polymerization, in which, for example, mixed monomer solution and radical initiator are metered into a reactor to allow the reaction for approximately over 4 hours and allowed to post-react for an additional 14 hours. The reaction temperature and time will be dependent on the initiator used. For example, for AIBN the reaction temperature is 70° C. and the time are as given above. The additives are then recovered by stripping off solvent followed by further drying, optionally under vacuum.

In one embodiment, the additive is formed using condensation polymerization, in which, for example, a diisocyanate is allowed to react with biocidally active monomer(s) containing an active hydrogen which are reactive with isocyanate groups, such as an alcohol, diols or monools, or diamines or monoamines, or thiols or dithiols, and combinations thereof (or other active hydrogen groups known to those skilled in the art) to form a prepolymer with free terminal isocyanate groups. A silicone or fluorocarbon-based monomer, such as monofunctional fluorinated or siloxane monomers, which contain active hydrogen groups which can react with isocyanate groups can then be reacted with the prepolymers to prepare oligomeric or polymeric additives with urethane and/or urea bonds. Useful polyisocyanates include H12MDI, MDI, HDI, TDI, IPDI, LDI, BDI, PDI, CHDI, TODI, and NDI.

Alternatively, the diisocynate can be initially reacted with a monofunctional fluorocarbon or siloxane active hydrogen containing monomer to form a reactive intermediate which contains a terminal isocyanate group which is further reacted with an active hydrogen containing antimicrobial monomer to produce an oligomeric or polymeric additive. Optionally, chain extenders and/or polyols can be included in these urethane-based additives. If desired, an excess of isocyanate can be used in the initial step of producing the urethane-based additive and the excess isocyanate can optionally be removed by distillation. In a further embodiment, the active hydrogen monomers of both the antimicrobial and fluorocarbon or silicone, can be combined with the diisocyanate, all at the same time, to produce the antimicrobial oligomeric or polymeric additive. Molecular weight of the antimicrobial additives can be controlled in the urethane-based additives by use of monofunctional reactants or by control of stoichiometry in ways that are well-known by those familiar with urethane chemistry.

Examples of biocidal monomers include, but are not limited to, polyhexamethylene biguanide partial free base which has been shown to react with isocyanates to give biguanidinoureas, as described in U.S. Pat. No. 7,771,743 or hydroxyl or dihydroxy biguanide compounds such as the reaction product of ethanolamine hydrochloride with the appropriate alkyl cyanoguanidino compound to give hydroxy biguanide compounds such as those shown below:

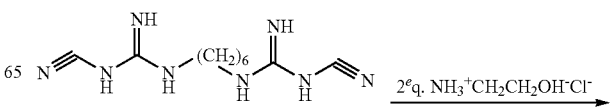

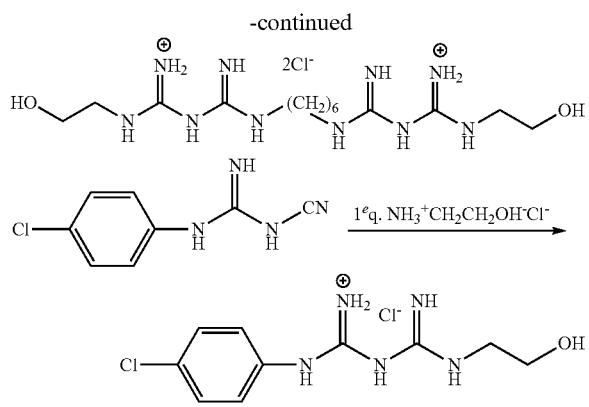

Other monomers which are reactive with isocyanates and which contain biocidal groups and which are known to those skilled in the art can be used in place of or in addition to the monomers disclosed above.

The Base Polymer

The biocidally active polymer compositions described herein include a base polymer. In some embodiments, the base polymer includes a thermoplastic polyurethane, a nylon, a polyethylene, a polyester, a polyvinylchloride, a polysulfone, a polysiloxane, a polypropylene, a polycarbonate, a polyether sulfone, a polyether ether ketone (PEEK), a polycaprolactone, a polydioxanol, a poly(1,3-trimethylene carbonate), a polytyrosine carbonate, a polyacrylate, a polymethacrylate, polylactic acid, polyglycolic acid, polyether block amide, copolymers thereof, and combinations thereof.

In one embodiment, the base polymer is a thermoplastic polyurethane. The TPU compositions described herein are made using: (a) a polyisocyanate; (b) a polyol; and optionally (a chain extender). The TPU may be present in the biocidally active polymer in an amount from about 80 to about 99.9 wt percent.

The Polyisocyanate

The compositions described herein are made using a) a polyisocyanate component. The polyisocyanate and/or polyisocyanate component includes one or more polyisocyanates. In some embodiments, the polyisocyanate component includes one or more diisocyanates.

In some embodiments, the polyisocyanate and/or polyisocyanate component includes an α, ω-alkylene diisocyanate having from 5 to 20 carbon atoms.

Suitable polyisocyanates include aromatic diisocyanates, aliphatic diisocyanates, or combinations thereof. In some embodiments, the polyisocyanate component includes one or more aromatic diisocyanates. In some embodiments, the polyisocyanate component is essentially free of, or even completely free of, aliphatic diisocyanates. In other embodiments, the polyisocyanate component includes one or more aliphatic diisocyanates. In some embodiments, the polyisocyanate component is essentially free of, or even completely free of, aromatic diisocyanates.

Examples of useful polyisocyanates include aromatic diisocyanates such as 4,4'-methylenebis(phenyl isocyanate) (MDI), m-xylene diisocyanate (XDI), phenylene-1,4-diisocyanate, naphthalene-1,5-diisocyanate, and toluene diisocyanate (TDI); as well as aliphatic diisocyanates such as isophorone diisocyanate (IPDI), 1,4-cyclohexyl diisocyanate (CHDI), decane-1,10-diisocyanate, lysine diisocyanate (LDI), 1,4-butane diisocyanate (BDI), isophorone diisocyanate (PDI), 3,3'-dimethyl-4,4'-biphenylene diisocyanate (TODI), 1,5-naphthalene diisocyanate (NDI), and dicyclohexylmethane-4,4'-diisocyanate (H12MDI). Mixtures of two or more polyisocyanates may be used. In some embodiments, the polyisocyanate is MDI and/or H12MDI. In some embodiments, the polyisocyanate includes MDI. In some embodiments, the polyisocyanate includes H12MDI.

In some embodiments, the thermoplastic polyurethane is prepared with a polyisocyanate component that includes H12MDI. In some embodiments, the thermoplastic polyurethane is prepared with a polyisocyanate component that consists essentially of H12MDI. In some embodiments, the thermoplastic polyurethane is prepared with a polyisocyanate component that consists of H12MDI.

In some embodiments, the thermoplastic polyurethane is prepared with a polyisocyanate component that includes (or consists essentially of, or even consists of) H12MDI and at least one of MDI, HDI, TDI, IPDI, LDI, BDI, PDI, CHDI, TODI, and NDI.

In some embodiments, the polyisocyanate used to prepare the TPU and/or TPU compositions described herein is at least 50%, on a weight basis, a cycloaliphatic diisocyanate. In some embodiments, the polyisocyanate includes an α, ω-alkylene diisocyanate having from 5 to 20 carbon atoms.

In some embodiments, the polyisocyanate used to prepare the TPU and/or TPU compositions described herein includes hexamethylene-1,6-diisocyanate, 1,12-dodecane diisocyanate, 2,2,4-trimethyl-hexamethylene diisocyanate, 2,4,4-trimethyl-hexamethylene diisocyanate, 2-methyl-1,5-pentamethylene diisocyanate, or combinations thereof.

The Polyol Component

The TPU compositions described herein are made using: (b) a polyol component.

Polyols include polyether polyols, polyester polyols, polycarbonate polyols, polysiloxane polyols, and combinations thereof.

Suitable polyols, which may also be described as hydroxyl terminated intermediates, when present, may include one or more hydroxyl terminated polyesters, one or more hydroxyl terminated polyethers, one or more hydroxyl terminated polycarbonates, one or more hydroxyl terminated polysiloxanes, or mixtures thereof.

Suitable hydroxyl terminated polyester intermediates include linear polyesters having a number average molecular weight (Mn) of from about 500 to about 10,000, from about 700 to about 5,000, or from about 700 to about 4,000, and generally have an acid number less than 1.3 or less than 0.5. The molecular weight is determined by assay of the terminal functional groups and is related to the number average molecular weight. The polyester intermediates may be produced by (1) an esterification reaction of one or more glycols with one or more dicarboxylic acids or anhydrides or (2) by transesterification reaction, i.e., the reaction of one or more glycols with esters of dicarboxylic acids. Mole ratios generally in excess of more than one mole of glycol to acid are preferred so as to obtain linear chains having a preponderance of terminal hydroxyl groups. Suitable polyester intermediates also include various lactones such as polycaprolactone typically made from ε-caprolactone and a bifunctional initiator such as diethylene glycol. The dicarboxylic acids of the desired polyester can be aliphatic, cycloaliphatic, aromatic, or combinations thereof. Suitable dicarboxylic acids which may be used alone or in mixtures generally have a total of from 4 to 15 carbon atoms and include: succinic, glutaric, adipic, pimelic, suberic, azelaic, sebacic, dodecanedioic, isophthalic, terephthalic, cyclohexane dicarboxylic, and the like. Anhydrides of the above dicarboxylic acids such as phthalic anhydride, tetrahydrophthalic anhydride, or the like, can also be used. Adipic acid is a preferred acid. The glycols which are reacted to form a desirable polyester intermediate can be aliphatic, aromatic, or combinations thereof, including any of the glycols described above in the chain extender section, and have a total of from 2 to 20 or from 2 to 12 carbon atoms. Suitable examples include ethylene glycol, 1,2-propanediol, 1,3-propanediol, 1,3-butanediol, 1,4-butanediol, 1,5-pentanediol, 1,6-hexanediol, 2,2-dimethyl-1,3-propanediol, 1,4-cyclohexanedimethanol, decamethylene glycol, dodecamethylene glycol, and mixtures thereof.

The polyol component may also include one or more polycaprolactone polyester polyols. The polycaprolactone polyester polyols useful in the technology described herein include polyester diols derived from caprolactone monomers. The polycaprolactone polyester polyols are terminated by primary hydroxyl groups. Suitable polycaprolactone polyester polyols may be made from ε-caprolactone and a bifunctional initiator such as diethylene glycol, 1,4-butanediol, or any of the other glycols and/or diols listed herein. In some embodiments, the polycaprolactone polyester polyols are linear polyester diols derived from caprolactone monomers.

Useful examples include CAPA™ 2202A, a 2,000 number average molecular weight (Mn) linear polyester diol, and CAPA™ 2302A, a 3,000 Mn linear polyester diol, both of which are commercially available from Perstorp Polyols Inc. These materials may also be described as polymers of 2-oxepanone and 1,4-butanediol.

The polycaprolactone polyester polyols may be prepared from 2-oxepanone and a diol, where the diol may be 1,4-butanediol, diethylene glycol, monoethylene glycol, 1,6-hexanediol, 2,2-dimethyl-1,3-propanediol, or any combination thereof. In some embodiments, the diol used to prepare the polycaprolactone polyester polyol is linear. In some embodiments, the polycaprolactone polyester polyol is prepared from 1,4-butanediol. In some embodiments, the polycaprolactone polyester polyol has a number average molecular weight from 500 to 10,000, or from 500 to 5,000, or from 1,000 or even 2,000 to 4,000 or even 3,000.

Suitable hydroxyl terminated polyether intermediates include polyether polyols derived from a diol or polyol having a total of from 2 to 15 carbon atoms, in some embodiments an alkyl diol or glycol which is reacted with an ether comprising an alkylene oxide having from 2 to 6 carbon atoms, typically ethylene oxide or propylene oxide or mixtures thereof. For example, hydroxyl functional polyether can be produced by first reacting propylene glycol with propylene oxide followed by subsequent reaction with ethylene oxide. Primary hydroxyl groups resulting from ethylene oxide are more reactive than secondary hydroxyl groups and thus are preferred. Useful commercial polyether polyols include poly(ethylene glycol) comprising ethylene oxide reacted with ethylene glycol, poly(propylene glycol) comprising propylene oxide reacted with propylene glycol, poly(tetramethylene ether glycol) comprising water reacted with tetrahydrofuran which can also be described as polymerized tetrahydrofuran, and which is commonly referred to as PTMEG. In some embodiments, the polyether intermediate includes PTMEG. Suitable polyether polyols also include polyamide adducts of an alkylene oxide and can include, for example, ethylenediamine adduct comprising the reaction product of ethylenediamine and propylene oxide, diethylenetriamine adduct comprising the reaction product of diethylenetriamine with propylene oxide, and similar polyamide type polyether polyols. Copolyethers can also be utilized in the described compositions. Typical copolyethers include the reaction product of THF and ethylene oxide or THF and propylene oxide. These are available from BASF as PolyTHF® B, a block copolymer, and PolyTHF® R, a random copolymer. The various polyether intermediates generally have a number average molecular weight (Mn) as determined by assay of the terminal functional groups which is an average molecular weight greater than about 700, such as from about 700 to about 10,000, from about 1,000 to about 5,000, or from about 1,000 to about 2,500. In some embodiments, the polyether intermediate includes a blend of two or more different molecular weight polyethers, such as a blend of 2,000 Mn and 1,000 Mn PTMEG.

Suitable hydroxyl terminated polycarbonates include those prepared by reacting a glycol with a carbonate. U.S. Pat. No. 4,131,731 is hereby incorporated by reference for its disclosure of hydroxyl terminated polycarbonates and their preparation. Such polycarbonates are linear and have terminal hydroxyl groups with essential exclusion of other terminal groups. The essential reactants are glycols and carbonates. Suitable glycols are selected from cycloaliphatic and aliphatic diols containing 4 to 40, and or even 4 to 12 carbon atoms, and from polyoxyalkylene glycols containing 2 to 20 alkoxy groups per molecule with each alkoxy group containing 2 to 4 carbon atoms. Suitable diols include aliphatic diols containing 4 to 12 carbon atoms such as 1,4-butanediol, 1,5-pentanediol, neopentyl glycol, 1,6-hexanediol, 2,2,4-trimethyl-1,6-hexanediol, 1,10-decanediol, hydrogenated dilinoleylglycol, hydrogenated dioleylglycol, 3-methyl-1,5-pentanediol; and cycloaliphatic diols such as 1,3-cyclohexanediol, 1,4-dimethylolcyclohexane, 1,4-cyclohexanediol-, 1,3-dimethylolcyclohexane-, 1,4-endomethylene-2-hydroxy-5-hydroxymethyl cyclohexane, and polyalkylene glycols. The diols used in the reaction may be a single diol or a mixture of diols depending on the properties desired in the finished product. Polycarbonate intermediates which are hydroxyl terminated are generally those known to the art and in the literature. Suitable carbonates are selected from alkylene carbonates composed of a 5 to 7 member ring. Suitable carbonates for use herein include ethylene carbonate, trimethylene carbonate, tetramethylene carbonate, 1,2-propylene carbonate, 1,2-butylene carbonate, 2,3-butylene carbonate, 1,2-ethylene carbonate, 1,3-pentylene carbonate, 1,4-pentylene carbonate, 2,3-pentylene carbonate, and 2,4-pentylene carbonate. Also, suitable herein are dialkylcarbonates, cycloaliphatic carbonates, and diarylcarbonates. The dialkylcarbonates can contain 2 to 5 carbon atoms in each alkyl group and specific examples thereof are diethylcarbonate and dipropylcarbonate. Cycloaliphatic carbonates, especially dicycloaliphatic carbonates, can contain 4 to 7 carbon atoms in each cyclic structure, and there can be one or two of such structures. When one group is cycloaliphatic, the other can be either alkyl or aryl. On the other hand, if one group is aryl, the other can be alkyl or cycloaliphatic. Examples of suitable diarylcarbonates, which can contain 6 to 20 carbon atoms in each aryl group, are diphenylcarbonate, ditolylcarbonate, and dinaphthylcarbonate.

Suitable polysiloxane polyols include α-ω-hydroxyl or amine or carboxylic acid or thiol or epoxy terminated polysiloxanes. Examples include poly(dimethysiloxane) terminated with a hydroxyl or amine or carboxylic acid or thiol or epoxy group. In some embodiments, the polysiloxane polyols are hydroxyl terminated polysiloxanes. In some embodiments, the polysiloxane polyols have a number-average molecular weight in the range from 300 to 5,000, or from 400 to 3,000.

Polysiloxane polyols may be obtained by the dehydrogenation reaction between a polysiloxane hydride and an aliphatic polyhydric alcohol or polyoxyalkylene alcohol to introduce the alcoholic hydroxy groups onto the polysiloxane backbone.

In some embodiments, the polysiloxane polyols may be represented by one or more compounds having the following formula:

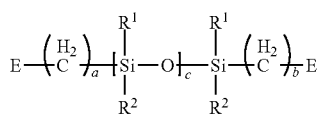

in which: each R1 and R2 are independently a 1 to 4 carbon atom alkyl group, a benzyl, or a phenyl group; each E is OH or $NHR^3$ where $R^3$ is hydrogen, a 1 to 6 carbon atoms alkyl group, or a 5 to 8 carbon atoms cyclo-alkyl group; a and b are each independently an integer from 2 to 8; c is an integer from 3 to 50. In amino-containing polysiloxanes, at least one of the E groups is $NHR^3$. In the hydroxyl-containing polysiloxanes, at least one of the E groups is OH. In some embodiments, both $R^1$ and $R^2$ are methyl groups.

Suitable examples include α,ω-hydroxypropyl terminated poly(dimethysiloxane) and α,ω-amino propyl terminated poly(dimethysiloxane), both of which are commercially available materials. Further examples include copolymers of the poly(dimethysiloxane) materials with a poly(alkylene oxide).

The polyol component, when present, may include poly(ethylene glycol), poly(tetramethylene ether glycol), poly(trimethylene oxide), ethylene oxide capped poly(propylene glycol), poly(butylene adipate), poly(ethylene adipate), poly(hexamethylene adipate), poly(tetramethylene-co-hexamethylene adipate), poly(3-methyl-1,5-pentamethylene adipate), polycaprolactone diol, poly(hexamethylene carbonate) glycol, poly(pentamethylene carbonate) glycol, poly(trimethylene carbonate) glycol, dimer fatty acid based polyester polyols, vegetable oil based polyols, or any combination thereof.

Examples of dimer fatty acids that may be used to prepare suitable polyester polyols include Priplast™ polyester glycols/polyols commercially available from Croda and Radia® polyester glycols commercially available from Oleon.

In some embodiments, the polyol component includes a polyether polyol, a polycarbonate polyol, a polycaprolactone polyol, or any combination thereof.

In some embodiments, the polyol component includes a polyether polyol. In some embodiments, the polyol component is essentially free of or even completely free of polyester polyols. In some embodiments, the polyol component used to prepare the TPU is substantially free of, or even completely free of polysiloxanes.

In some embodiments, the polyol component includes oligomeric polyethylene oxide, polypropylene oxide, polybutylene oxide, polystyrene oxide, poly(tetramethylene ether glycol), poly(propylene glycol), poly(ethylene glycol), copolymers of poly(ethylene glycol) and poly(propylene glycol), epichlorohydrin, and the like, or combinations thereof. In some embodiments the polyol component includes poly(tetramethylene ether glycol).

The Chain Extender

The TPU compositions described herein are made using c) a chain extender component. Chain extenders include diols, diamines, and combination thereof.

Suitable chain extenders include relatively small polyhydroxy compounds, for example lower aliphatic or short chain glycols having from 2 to 20, or 2 to 12, or 2 to 10 carbon atoms. Suitable examples include ethylene glycol, diethylene glycol, propylene glycol, dipropylene glycol, 1,4-butanediol (BDO), 1,6-hexanediol (HDO), 1,3-butanediol, 1,5-pentanediol, neopentylglycol, 1,4-cyclohexanedimethanol (CHDM), 2,2-bis[4-(2-hydroxyethoxy) phenyl] propane (HEPP), hexamethylenediol, heptanediol, nonanediol, dodecanediol, 3-methyl-1,5-pentanediol, ethylenediamine, butanediamine, hexamethylenediamine, and hydroxyethyl resorcinol (HER), and the like, as well as mixtures thereof. In some embodiments the chain extender includes BDO, HDO, 3-methyl-1,5-pentanediol, or a combination thereof. In some embodiments, the chain extender includes BDO. Other glycols, such as aromatic glycols could be used, but in some embodiments the TPUs described herein are essentially free of or even completely free of such materials.

In some embodiments, the chain extender used to prepare the TPU is substantially free of, or even completely free of, 1,6-hexanediol. In some embodiments, the chain extender used to prepare the TPU includes a cyclic chain extender. Suitable examples include CHDM, HEPP, HER, and combinations thereof. In some embodiments, the chain extender used to prepare the TPU includes an aromatic cyclic chain extender, for example HEPP, HER, or a combination thereof. In some embodiments, the chain extender used to prepare the TPU includes an aliphatic cyclic chain extender, for example CHDM. In some embodiments, the chain extender used to prepare the TPU is substantially free of, or even completely free of aromatic chain extenders, for example aromatic cyclic chain extenders. In some embodiments, the chain extender used to prepare the TPU is substantially free of, or even completely free of polysiloxanes.

In some embodiments, the chain extender component includes 1,4-butanediol, 2-ethyl-1,3-hexanediol, 2,2,4-trimethyl pentane-1,3-diol, 1,6-hexanediol, 1,4-cyclohexane dimethylol, 1,3-propanediol, 3-methyl-1,5-pentanediol or combinations thereof. In some embodiments, the chain extender component includes 1,4-butanediol, 3-methyl-1,5-pentanediol or combinations thereof. In some embodiments, the chain extender component includes 1,4-butanediol.

The described compositions include the TPU materials described above and also TPU compositions that include such TPU materials and one or more additional components. These additional components include other polymeric materials that may be blended with the TPU described herein. These additional components also include one or more additives that may be added to the TPU, or blend containing the TPU, to impact the properties of the composition.

The TPU described herein may also be blended with one or more other polymers. The polymers with which the TPU described herein may be blended are not overly limited. In some embodiments, the described compositions include two or more of the described TPU materials. In some embodiments, the compositions include at least one of the described TPU materials and at least one other polymer, which is not one of the described TPU materials. In some embodiments, the described blends will have the same combination of properties described above for the TPU composition. In other embodiments, the TPU composition will of course have the described combination of properties, while the blend of the TPU composition with one or more of the other polymeric materials described above may or may not.

Polymers that may be used in combination with the TPU materials described herein also include more conventional TPU materials such as non-caprolactone polyester-based TPU, polyether-based TPU, or TPU containing both non-caprolactone polyester and polyether groups. Other suitable materials that may be blended with the TPU materials described herein include polycarbonates, polyolefins, styrenic polymers, acrylic polymers, polyoxymethylene polymers, polyamides, polyphenylene oxides, polyphenylene sulfides, polyvinylchlorides, chlorinated polyvinyl chlorides, polylactic acids, or combinations thereof.

Polymers for use in the blends described herein include homopolymers and copolymers. Suitable examples include: (i) a polyolefin (PO), such as polyethylene (PE), polypropylene (PP), polybutene, ethylene propylene rubber (EPR), polyoxyethylene (POE), cyclic olefin copolymer (COC), or combinations thereof; (ii) a styrenic, such as polystyrene (PS), acrylonitrile butadiene styrene (ABS), styrene acrylonitrile (SAN), styrene butadiene rubber (SBR or HIPS), polyalphamethylstyrene, styrene maleic anhydride (SMA), styrene-butadiene copolymer (SBC) (such as styrene-butadiene-styrene copolymer (SBS) and styrene-ethylene/butadiene-styrene copolymer (SEBS)), styrene-ethylene/propylene-styrene copolymer (SEPS), styrene butadiene latex (SBL), SAN modified with ethylene propylene diene monomer (EPDM) and/or acrylic elastomers (for example, PS-SBR copolymers), or combinations thereof; (iii) a thermoplastic polyurethane (TPU) other than those described above; (iv) a polyamide, such as Nylon™, including polyamide 6,6(PA66), polyamide 1,1(PA11), polyamide 1,2 (PA12), a copolyamide (COPA), or combinations thereof; (v) an acrylic polymer, such as polymethyl acrylate, polymethylmethacrylate, a methyl methacrylate styrene (MS) copolymer, or combinations thereof; (vi) a polyvinylchloride (PVC), a chlorinated polyvinylchloride (CPVC), or combinations thereof; (vii) a polyoxyemethylene, such as polyacetal; (viii) a polyester, such as polyethylene terephthalate (PET), polybutylene terephthalate (PBT), copolyesters and/or polyester elastomers (COPE) including polyetherester block copolymers such as glycol modified polyethylene terephthalate (PETG), polylactic acid (PLA), polyglycolic acid (PGA), copolymers of PLA and PGA, or combinations thereof; (ix) a polycarbonate (PC), a polyphenylene sulfide (PPS), a polyphenylene oxide (PPO), or combinations thereof; or combinations thereof.

In some embodiments, these blends include one or more additional polymeric materials selected from groups (i), (iii), (vii), (viii), or some combination thereof. In some embodiments, these blends include one or more additional polymeric materials selected from group (i). In some embodiments, these blends include one or more additional polymeric materials selected from group (iii). In some embodiments, these blends include one or more additional polymeric materials selected from group (vii). In some embodiments, these blends include one or more additional polymeric materials selected from group (viii).

The additional additives suitable for use in the TPU compositions described herein are not overly limited. Suitable additives include pigments, UV stabilizers, UV absorbers, antioxidants, lubricity agents, heat stabilizers, hydrolysis stabilizers, cross-linking activators, flame retardants, layered silicates, fillers, colorants, reinforcing agents, adhesion mediators, impact strength modifiers, antimicrobials, radiopaque additives, for example, barium sulfate, bismuth subcarbonate, bismuth trioxide, bismuth oxychloride, tantalum, and tungsten, amongst others, and any combination thereof.

In some embodiments, the additional component is a flame retardant. Suitable flame retardants are not overly limited and may include a boron phosphate flame retardant, a magnesium oxide, a dipentaerythritol, a polytetrafluoroethylene (PTFE) polymer, or any combination thereof. In some embodiments, this flame retardant may include a boron phosphate flame retardant, a magnesium oxide, a dipentaerythritol, or any combination thereof. A suitable example of a boron phosphate flame retardant is BUDIT®-326, commercially available from Budenheim USA, Inc. When present, the flame retardant component may be present in an amount from 0 to 10 weight percent of the overall TPU composition, in other embodiments from 0.5 to 10, or from 1 to 10, or from 0.5 or 1 to 5, or from 0.5 to 3, or even from 1 to 3 weight percent of the overall TPU composition.

The TPU compositions described herein may also include additional additives, which may be referred to as a stabilizer. The stabilizers may include antioxidants such as phenolics, phosphites, thioesters, and amines, light stabilizers such as hindered amine light stabilizers and benzothiazole UV absorbers, and other process stabilizers and combinations thereof. In one embodiment, the preferred stabilizer is Irganox®-1010 from BASF and Naugard®-445 from Chemtura. The stabilizer is used in the amount from about 0.1 weight percent to about 5 weight percent, in another embodiment from about 0.1 weight percent to about 3 weight percent, and in another embodiment from about 0.5 weight percent to about 1.5 weight percent of the TPU composition.

In addition, various conventional inorganic flame retardant components may be employed in the TPU composition. Suitable inorganic flame retardants include any of those known to one skilled in the art, such as metal oxides, metal oxide hydrates, metal carbonates, ammonium phosphate, ammonium polyphosphate, calcium carbonate, antimony oxide, clay, mineral clays including talc, kaolin, wollastonite, nanoclay, montmorillonite clay which is often referred to as nano-clay, and mixtures thereof. In one embodiment, the flame retardant package includes talc. The talc in the flame retardant package promotes properties of high limiting oxygen index (LOI). The inorganic flame retardants may be used in the amount from 0 to about 30 weight percent, from about 0.1 weight percent to about 20 weight percent, in another embodiment about 0.5 weight percent to about 15 weight percent of the total weight of the TPU composition.

Still further optional additives may be used in the TPU compositions described herein. The additives include colorants, antioxidants (including phenolics, phosphites, thioesters, and/or amines), antiozonants, stabilizers, inert fillers, lubricants, inhibitors, hydrolysis stabilizers, light stabilizers, hindered amines light stabilizers, benzotriazole UV absorber, heat stabilizers, stabilizers to prevent discoloration, dyes, pigments, inorganic and organic fillers, reinforcing agents, radio-opacifiers (for example $BaSO_4$), and combinations thereof.

All of the additives described above may be used in an effective amount customary for these substances. The non-flame retardants additives may be used in amounts of from about 0 to about 30 weight percent, in one embodiment from about 0.1 to about 25 weight percent, and in another embodiment about 0.1 to about 20 weight percent of the total weight of the TPU composition.

These additional additives can be incorporated into the components of, or into the reaction mixture for, the preparation of the TPU resin, or after making the TPU resin. In another process, all the materials can be mixed with the TPU resin and then melted or they can be incorporated directly into the melt of the TPU resin.

The thermoplastic polyurethanes of the invention can be prepared by processes which are conventional in the art for the synthesis of polyurethane elastomers such as but not limited to a batch process or a one-shot technique. In the batch process, the components, i.e., the diisocyanate(s), the polyol(s), and the chain extenders (s), as well as the catalyst(s) and any other additive(s), if desired, are introduced into a container, mixed, dispensed into trays and allowed to cure. The cured TPU can then be granulated and pelletized. The one-shot procedure is performed in an extruder, e.g. single screw, twin screw, wherein the formative components, introduced individually or as a mixture into the extruder, and reacted at a temperature generally in one embodiment from about 100° C. to about 300° C., and in another embodiment from about 150° C. to about 250° C., and even from about 150° C. to about 240° C.

One or more polymerization catalysts may be present during the polymerization reaction. Generally, any conventional catalyst can be utilized to react the diisocyanate with the polyol intermediates or the chain extender. Examples of suitable catalysts which in particular accelerate the reaction between the NCO groups of the diisocyanates and the hydroxy groups of the polyols and chain extenders are the conventional tertiary amines known from the prior art, e.g. triethylamine, dimethylcyclohexylamine, N-methylmorpholine, N,N'-dimethylpiperazine, 2-(dimethylaminoethoxy) ethanol, diazabicyclo[2.2.2]octane and the like, and also in particular organometallic compounds, such as titanic esters, iron compounds, e.g. ferric acetylacetonate, tin compounds, e.g. stannous diacetate, stannous dioctoate, stannous dilaurate, or the dialkyltin salts of aliphatic carboxylic acids, e.g. dibutyltin diacetate, dibutyltin dilaurate, or the like. The amounts usually used of the catalysts are from 0.0001 to 0.1 part by weight per 100 parts by weight of polyhydroxy compound (b).

The process may further include the step of: mixing the TPU composition with one or more blend components, including one or more additional TPU materials and/or polymers, including any of those described above.

The process may further include the step of: mixing the TPU composition of step (I) with one or more additional additives selected from the group consisting of pigments, UV stabilizers, UV absorbers, antioxidants, lubricity agents, heat stabilizers, hydrolysis stabilizers, cross-linking activators, flame retardants, layered silicates, fillers, colorants, reinforcing agents, adhesion mediators, impact strength modifiers, and antimicrobials.

The process may further include the step of: mixing the TPU composition with one or more blend components, including one or more additional TPU materials and/or polymers, including any of those described above, and/or the step of: mixing the TPU composition with one or more additional additives selected from the group consisting of pigments, UV stabilizers, UV absorbers, antioxidants, lubricity agents, heat stabilizers, hydrolysis stabilizers, cross-linking activators, flame retardants, layered silicates, fillers, colorants, reinforcing agents, adhesion mediators, impact strength modifiers, radio-opacifiers, and antimicrobials.

Preparation of the Biocidally Active Polymer Compositions

The biocidally active polymer compositions may be prepared by melt mixing of the additive into the polymer, incorporation of the additive during polymer synthesis, coagulating or dissolving the additive and base polymer in a common solvent and casting, coagulating, or electrospinning the solvent mixture containing the additive and the base polymer casting, or electrospinning a solvent mixture containing the additive and the polymer.

In some embodiments, where the base polymer is a TPU, and where the antimicrobial additives are incorporated during polymer synthesis, the diisocyanate, polyols and chain extender, which are reacted together to form the TPU, are mixed together either with or without catalysts, depending on the type of TPU being used. During the reaction, the polymeric or oligomeric surface modifying additives are preheated and poured into the reaction mixture. The resulting surface-modified TPU polymer can then be cut into pieces and granulated for extrusion, injection molding, thermoforming, compression molding processes, or any of a variety of other processes commonly used for the processing of polymers.

The biocidally active polymer compositions may alternately be prepared by melt mixing of the oligomeric or polymeric additives using a using a Brabender Plasticorder with the mixing bowl attachment. In some embodiments, the blends are run with the additives and the TPU are mixed as a mixture of solids (salt and pepper) prior to melt mixing. In some embodiments, the additive may be added to the base polymer following the initial charge of the base TPU had melted and the torque had stabilized. Alternatively, a twin screw extruder or other melt mixing apparatus can be used to melt mix the additive into the TPU via typical methods know to those skilled in the art. In embodiments where the biocidally active polymer composition is produced by melt mixing or where it is melt processed after it is produced, it is necessary that the polymeric or oligomeric biocidal additive must be thermally stable at the temperatures required for this processing.

In one embodiment, the polymer composition may be coated onto a material. The material may include a polymer, a glass, a ceramic, a metal, or a composite. The method of application of the coating is not overly limited, and can include dip coating, spray coating, roll-to-roll coating or spin coating. The coating may be applied at a thickness of from about 1 micrometer to about 200 micrometers, or from about 5 micrometers to about 100 micrometers. The coated polymer may then be dried in an oven for approximately 24 hours, and in some embodiments at 80° C. In some embodiments, following coating of the base polymer, a further step of annealing may be performed, as described below.

In some embodiments, the polymer compositions may be printed on a material forming an article. The printing methods are not overly limited, and may include such methods as additive manufacturing, digital printing, and the like, as well as other printing methods known to those skilled in the art.

In a further embodiment, the polymer compositions may include a further processing step in which the compositions are annealed. In one embodiment, annealing may be accomplished in an oven at temperature of from about 30° C. up to about 150° C., or from about 50° C. to about 80° C. In some embodiments, annealing can occur for periods of from about two hours up to about seventy-two hours, or from 24 hours to 48 hours. In one embodiment, the annealing period may be for a period of at least 2 hours, or at least 12 hours, or at least 24 hours. In some embodiments, the annealing step takes place by exposing the polymer composition to solvent vapors, optionally at temperatures above ambient.

The polymer materials and/or compositions described herein may be used in the preparation of one or more articles. The specific type of articles that may be made from the polymer materials and/or compositions described herein are not overly limited. In general, the polymer materials and/or compositions described herein may be used in any application where a biocidally active or biocidally active and non-fouling surface is desired.

The invention further provides an article made with the surface-modified polymer materials and/or compositions described herein. In some embodiments, the article may include a medical device. Examples include but are not limited to medical applications, for example, where the polymer described herein may be used in angiography catheters, angioplasty catheters, urology catheters, dialysis catheters, Swan-Ganz catheters central venous catheters, and peripherally inserted central catheters; catheter connectors; dialysis membranes; medical tubing; wound care articles, including wound closures, staples, sutures, meshes, buttressing devices, suture reinforcements, wound care dressings, and the like; orthopedic articles including nails, screws, plates, cages, prosthetics and the like; neural implants, including drains, shunts, and the like; implants, including dental implants, ocular implants, cochlear implants, breast implants, and the like; a heart valve, a heart by-pass machine, an extracorporeal blood device, a nerve conduit, a vascular graft, a stent, a contact lens, and the like; as well as used in, personal care applications, pharmaceutical applications, health care product applications, marine applications, or any other number of applications. In some embodiments, these articles are prepared by extruding, injection molding, or any combination thereof.

The biocidally active polymer compositions as described herein can provide biocidal and biocidal/nonfouling/non-thrombogenic properties to the article prepared with the composition. In some embodiments, the polymer composition provides a reduction in microbial activity of at least 90% or at least 95%, or up to 99% and greater, or from 90% up to 99% and above. In some embodiments, the polymer composition provides a reduction in protein absorption of at least 50%, or at least 60%, or 70%.

The amount of each chemical component described is presented exclusive of any solvent which may be customarily present in the commercial material, that is, on an active chemical basis, unless otherwise indicated. However, unless otherwise indicated, each chemical or composition referred to herein should be interpreted as being a commercial grade material which may contain the isomers, by-products, derivatives, and other such materials which are normally understood to be present in the commercial grade.

It is known that some of the materials described above may interact in the final formulation, so that the components of the final formulation may be different from those that are initially added. For instance, metal ions (of, e.g., a flame retardant) can migrate to other acidic or anionic sites of other molecules. The products formed thereby, including the products formed upon employing the composition of the technology described herein in its intended use, may not be susceptible of easy description. Nevertheless, all such modifications and reaction products are included within the scope of the technology described herein; the technology described herein encompasses the composition prepared by admixing the components described above.

EXAMPLES

The technology described herein may be better understood with reference to the following non-limiting examples.

Materials

The materials are generally commercially available from chemical supply houses known to those skilled in the chemical arts or from the supplier indicated below.

| Name | Identity | Source |
|---|---|---|
| Capstone MA | 2-Methyl-2-propenoic acid, 3,3,4,4,5,5,6,6,7,7,8,8,8-tridecafluorooctyl ester | DuPont |
| TPU 1 | Aromatic polyether-based TPU | Lubrizol |
| TPU2 | Low melting aliphatic polyether-based TPU | Lubrizol |
| Desmodur ® W | bis(4-isocyanotocyclohexyl) methane | Bayer |
| AIBN | Azo-bis-isobutyronitrile | Sigma Aldrich |
| PQ6MA | n-hexyl dimethylamino methacrylate | Lubrizol |
| PEG MA | Poly(ethylene glycol) methyl ether methacrylate (M.W. approx. 500) | Sigma Aldrich |
| Capstone 62AL | 1,1,1,2,2,3,3,4,4,5,5,6,6-tridecafluorooctyl alcohol | DuPont |
| Ethanolamine HCl | Ethanolamine HCl | TCI |
| 1,6 biscyanoguandino hexane | 1,6 biscyanoguandino hexane | BOC chemical |
| p-Chlorophenyl-dicyandiamide | p-Chlorophenyldicyandiamide | BOC chemical |

Methacrylate Additives Synthesis

A reaction kettle is charged with solvent and preheated to desired temperature of 70° C. under nitrogen purge to remove any oxygen. Monomers and initiator are mixed with solvent in amounts as set forth in Table 1 and added into the reaction kettle via a syringe pump over a period of 3-4 hours. Monomer ratios and total monomer/initiator are varied to obtain additives with different compositions and molecular weights targeting approximately 2-15,000 Daltons. The reaction is kept at the reaction temperature (70° C. for AIBN initiator) for an additional 4 hours to consume most of the monomers and initiator (residual monomer is less than 1% as measured by NMR). Polymers for the PEG series are recovered by rotatory evaporation or precipitation in cold diethyl ether or acetone and further dried under vacuum.

TABLE 1

Additive compositions

| | Monomer (mole %) | | | | | |
|---|---|---|---|---|---|---|
| Example # | PQ6 MA | PEGMA | Capstone MA | Methyl MA | NMR** ratio | Mn*/ *PDI*** |
| INV EX1 | 30 | 0 | 30 | 40 | 32/0/30/38 | 5.8K/1.9 |

TABLE 1-continued

Additive compositions

| Example # | PQ6 MA | PEGMA | Capstone MA | Methyl MA | NMR** ratio | Mn*/ *PDI*** |
|---|---|---|---|---|---|---|
| INV EX2 | 30 | 0 | 10 | 60 | 33/0/ 12/55 | 4.3K/1.9 |
| INV EX 3 | 20 | 30 | 30 | 20 | 20/26/ 30/24 | 7.6K/1.9 |
| INV EX 4 | 10 | 30 | 30 | 30 | 10/28/ 29/33 | 7.1K/1.9 |

*Mn is estimated based on un-quaternized versions of the inventive additives.
**NMR ratio is the ratio of monomers in additive as measured by NMR
***PDI is polydispersity index Urethane Based Antimicrobial PHMB Additive Synthesis:

Polyhexamethylene biguanide hydrochloride [PHMB/HCl (33 g)] is dissolved in 100 ml of methanol (MeOH) and potassium hydroxide (KOH) (200 ml, 0.1M MeOH solution) is slowly added to the PHMB solution in a round bottomed flask. The reaction is allowed to run overnight and methanol is stripped off by rotvap and then vacuum pump. The PHMB (11 g) is dissolved in 150 g of Dimethyl sulfoxide (DMSO) and 1.67 g of Diphenylmethane diisocyanate (MDI) is added. The reaction is kept at 65° C. for 4 hours. Capstone 62MA (2.42 g) is added and the reaction is allowed to react for an additional 8 hours. Free NCO is 0.02%. The Inventive Additive 1 is recovered by precipitation in diethyl ether.

Synthesis of Hydroxyl Biguanide Monomers:

In an appropriately sized three neck round bottomed flask, cyanoguanidino reactant is combined with an equivalent amount of ethanolamine hydrochloride. The flask is purged with nitrogen and heated to 120° C. with stirring. After reacting for 8 hours, the reaction is cooled and the product is precipitated by addition of a non-solvent. After washing with the non-solvent, the monomer is analyzed by NMR to confirm completion of the reaction.

Urethane Based Antimicrobial Biguanide Diol based Additives Synthesis:

BGdiol (1,6-bis-hydroxyethylbiguanidino hexane) and 2 equivalents of Capstone 62Al are mixed in a can and preheated to 50° C., H12MDI, in an amount to achieve equivalent numbers of hydroxyl and isocyanate groups, is added with several drops of CoTin catalyst. An exothermic reaction is observed and the mixture is transferred to an oven once the reaction reaches 75° C. The mixture is further cured at 125° C. for 3 hours to yield the Inventive Additive 2.

Coating of TPU Film with Urethane Based Antimicrobial Polymer Composition:

The Inventive Additive 2 is dissolved in Dimethylformamide (DMF) and mixed with an aliphatic TPU solution to get coating solutions with additive/TPU (w/w) ratios of 4/96 and 6/94. The total solid content of the coating solutions is 2%. An aliphatic TPU coupon (5 cm×5 cm) is dip coated with the coating solution, dried and annealed in oven at 50° C. for 48 hours.

Antimicrobial Test (JIS Z2801 Protocol)

Film samples (approximately 35 mm×35 mm) were inoculated with 0.4 ml of a 0.2% nutrient broth seeded with a standardized culture of a test organism in triplicate. The inoculated samples were covered with an inert film and incubated at 36±2° C. in a humidity chamber for 24 hours. Surviving microorganisms were recovered via elution of the broth inoculum from the test sample into neutralizing broth. Microbial counts of the samples were determined and the log reduction of microorganisms (versus untreated samples) and antimicrobial activity were calculated.

Zone of Inhibition Protocol (AATCC 147 Protocol)

The parallel streak method is a qualitative screening test to demonstrate bacteriostatic (antimicrobial) activity of diffusible antimicrobials on treated textile surfaces. The scope of the test demonstrates bactericidal (inhibition of multiplication and growth) activity by diffusion of the antimicrobial agent through agar. The test sample (textile) is place in intimate contact with a nutrient agar surface which is streaked ("parallel streaks") with an inoculum of test organism. The samples are incubated for 18-24 hours at a temperature of 37±2° C., after which bacteriostatic activity is demonstrated by a clear area of interrupted growth underneath and along the sides of the test material.

Protein Fouling Test (Fluorescence Method)

A static test method for measuring protein adsorption on the surface of thermal processed TPUs. The method utilizes fluorescently labeled proteins to quantify the amount of protein adsorbed onto the surface of the TPU samples. The technique is similar to that as described by Hlady, et al, in *Methods for Studying Protein Adsorption*, p. 402-429, 1999, Methods in Enzymology and Ishihara, et al, *Why do Phospholipid Polymers Reduce Protein Adsorption*, Journal of Biomedical Materials Research, p. 323-330, 1998. Samples of the films from Table 2 are cut into (2.5 cm×0.6 cm) coupons and the coupons are washed by shaking in 1% sodium dodecyl sulfate (SDS) and then rinsed well with deionized water and 1X phosphate buffered saline (PBS). Each washed coupon is then placed into an amber 2 ml centrifuge tube containing either fluorescently labeled fibrinogen (Fbg) or bovine serum albumin (BSA) (Alexa Fluor 488 or Alexa Fluor 594 respectively, Molecular Probes, Eugene, Oreg.). The samples are incubated at 37° C. for 1 hour, after which the coupons are removed and washed with ~25 ml 1X PBS 3 times. Using a biopsy punch, a 4.0 mm punch of each coupon is collected and placed into a 2 ml amber tube containing 1.5 ml 1% SDS. The punches are vortex cleaned and allowed to soak until analysis. The SDS solutions are transferred to cuvettes and read directly on the fluorimeter. The amount of protein adsorbed onto the TPU surface (ng/cm$^2$) is calculated by correlating the absorbance of the fluorescently labeled protein to a standard curve and dividing by the surface area of the 4 mm punch.

The results of the antimicrobial testing is shown in Table 2.

TABLE 2

Antimicrobial test results of PQ6 additives

| Formulation | Process condition | E. coli (Log reduction) | S. aureus (Log reduction) | ZOI |
|---|---|---|---|---|
| TPU1* | Extrusion | 0 | 0 | 0 |
| Inv Ex 1 TPU1 | Dip coating | >5.93 | >4.22 | 0 |
| Inv Ex 2 1% TPU2 | Extrusion | >4.59 | >2.27 | 0 |
| Inv Ex 1 1% TPU2 | Com. Molding | >5.30 | >3.38 | 0 |
| Inv Ex 2 1% TPU1 | Extrusion | 3.36* | 2.71 | 0 |
| Inv Ex 1 1% TPU1 | Com. Molding | >5.56 | >3.88 | 0 |

*TPU1 is a control containing no inventive additive.

As can be seen in Table 2, the antimicrobial efficacy of the inventive examples is demonstrated as measured by log reduction of microbe of two bacterial strains for Films containing the inventive additives compared with a thermoplastic polyurethane Film with no inventive additive. Additionally, the zone of inhibition results indicates that there is no leaching of the inventive additive.

TABLE 3

Antimicrobial activity test* results for Urethane-based additives

| sample | E. Coli (log reduction) | S. Aureus (log reduction) |
|---|---|---|
| Inv Ex 5** | 0.18 | 1.68 |

*JIS Z2801 test method
**Additive 2 and aliphatic TPU

As can be seen in Table 3, the antimicrobial efficacy of the inventive example is demonstrated as measured by log reduction of microbe for two bacterial strains for a Film containing the urethane-based inventive additive.

TABLE 4

Antimicrobial and protein adsorption test

| Formulation | Process condition | Antimicrobial Test (log reduction) | | | Reduction in Protein Adsorption | |
|---|---|---|---|---|---|---|
| | | E. coli | S. aureus | ZOI | BSA | Fbg |
| INV EX 3 5% TPU2 | Com. Molding | >6 | >4.9 | 0 | 75% | 92% |
| INV EX 4 5% TPU2 | Com. Molding | >5.7 | >4.7 | 0 | 90% | 100% |

The results of the antimicrobial and fluorescent protein fouling test on the Film samples are shown in Table 4. It can be seen that the amount of protein adsorbed onto the surface of the Samples containing the inventive additives is significantly reduced compared to a base TPU with no inventive additive. The actual adsorption of the proteins is in the range that has been shown to be useful in non-thrombogenic, biocompatible medical devices. Additionally, it can be seen that there was a reduction in the antimicrobial activity as compared to a base TPU containing no inventive additive.

Annealing Testing

Samples of films from Table 1 are extruded or compression molded and hung inside an oven by a binder clip during a given time. The oven was heated to 80° C. and held for a period of 48 hours. The samples were then evaluated for antimicrobial efficacy according to the JIS Z2801 method. The antimicrobial activity of the additive composition was measured and results are indicated below:

TABLE 5

Annealing and antimicrobial activity

| Formulation | Process method | E. coli Log reduction | S. aureus Log reduction |
|---|---|---|---|
| INV EX 3 5% TPU2 | Com. Molding | >5.30 | >3.38 |
| INV EX 3 5% TPU2 2 day annealed | Com. Molding | >6.09 | >4.95 |

As can be seen in Table 5, the antimicrobial efficacy as measured by log reduction of microbe for Films containing the inventive additives following annealing of the Films is significantly increased compared to a Film containing the inventive additives which has not been subjected to the annealing process.

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the technology described herein can be used together with ranges or amounts for any of the other elements.

As described hereinafter the molecular weight of the materials described above have been determined using known methods, such as GPC analysis using polystyrene standards. Methods for determining molecular weights of polymers are well known. The methods are described for instance: (i) P. J. Flory, "Principles of star polymer Chemistry", Cornell University Press 91953), Chapter VII, pp 266-315; or (ii) "Macromolecules, an Introduction to star polymer Science", F. A. Bovey and F. H. Winslow, Editors, Academic Press (1979), pp 296-312. As used herein the weight average and number weight average molecular weights of the materials described are obtained by integrating the area under the peak corresponding to the material of interest, excluding peaks associated with diluents, impurities, uncoupled star polymer chains and other additives.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the basic and novel characteristics of the composition or method under consideration. That is "consisting essentially of" permits the inclusion of substances that do not materially affect the basic and novel characteristics of the composition under consideration.

While certain representative embodiments and details have been shown for the purpose of illustrating the subject technology described herein, it will be apparent to those skilled in this art that various changes and modifications can be made therein without departing from the scope of the subject invention. In this regard, the scope of the technology described herein is to be limited only by the following claims.

What is claimed is:

1. An anti-microbial polymer composition comprising:
   a) an oligomeric or polymeric additive formed from:
      (i) a biocidally active monomer or group comprising one or more of an acrylate, methacrylate, norbonene, vinyl or allyl monomer bearing one or more alkyl or aryl quarternized ammonium, guanidine groups, biguanidine groups, and any combination thereof;
      (ii) a bloom-promoting fluorocarbon monomer or group;
      (iii) optionally, an adhesion-promoting monomer or group;
      (iv) optionally, a bloom-promoting silicone monomer or group; and
   b) a thermoplastic polyurethane base polymer.

2. The anti-microbial polymer composition of claim 1, further comprising: a non-fouling monomer.

3. The anti-microbial polymer composition of claim 1, wherein the oligomeric or polymeric additive is derived from (i) a biocidally active acrylate, methacrylate, acrylamide or vinyl monomer; (ii) a bloom promoting fluorocarbon-based acrylate, methacrylate, acrylamide or vinyl monomer; (iii) optionally, an adhesion-promoting monomer or group; and (iv) optionally, a bloom-promoting silicone-based acrylate, methacrylate, norbornene, vinyl or allyl monomer.

4. The anti-microbial polymer composition of claim 1, wherein the oligomeric or polymeric additive is derived from (i) a silicone or fluorocarbon-based monomer containing an active hydrogen compound; (ii) a biocidally active monomer containing an active hydrogen; (iii) optionally, an adhesion-promoting monomer or group containing an active hydrogen; and (iv) a polyisocyanate.

5. The polymer of claim 1, wherein the oligomeric or polymeric additive is a random, a block, a graft or a branched polymer or copolymer.

6. The polymer composition of claim 1, wherein the oligomeric or polymeric additive is added to the base polymer to form a polymer blend.

7. The polymer composition of claim 3, wherein the biocidally active monomer comprises one or more of an acrylate, methacrylate, norbonene, vinyl or allyl monomer bearing one or more alkyl or aryl quarternized ammonium, sulfonium, orphosphonium groups, guanidine groups, biguanidine groups, or any combination thereof.

8. The polymer composition of claim 3, wherein the silicone monomer comprises an acrylate, methacrylate, norbornene, vinyl or allyl monomer bearing one or more polysiloxane and/or fluorocarbon groups.

9. The polymer composition of claim 3, wherein the adhesion-promoting monomer or group comprises an alkyl or other substituted methacrylate, acrylate or acrylamide monomer.

10. The polymer composition of claim 9, wherein the adhesion-promoting monomer comprises methyl methacrylate.

11. The polymer composition of claim 1, wherein the polymer composition is non-protein fouling and/or anti-thrombogenic.

12. The polymer of claim 11, wherein the non-fouling monomer comprises a zwitterionic monomer or a polyalkylene glycol monomer.

13. The polymer of claim 12, wherein the zwitterionic monomer comprises a phosphorylcholine, a carboxybetaine, or a sulfobetaine monomer.

14. The polymer of claim 1, wherein the molecular weight of the polymeric or oligomeric additive is from about 1,000 to about 50,000 daltons.

15. The polymer composition of claim 1, wherein the polymer composition provides a reduction in microbial activity of at least 90%.

16. The polymer composition of claim 1, wherein the polymer composition is melt processable or solution processable.

17. The polymer composition of claim 3, wherein the biocidally active monomer comprises polyhexamethylenebiguanide or p-chlorophenylguanidinoethoxymethacrylate.

18. The polymer composition of claim 3, wherein the bloom-promoting silicone or fluorocarbon-based monomer comprises 2-methyl-2-propenoic acid,3,3,4,4,5,5,6,6,7,7,8,8,8-tridecafluorooctyl ester.

19. The polymer composition of claim 4, wherein the polyisocyanate comprises a diisocyanate.

20. The polymer composition of claim 19, wherein the diisocyanate comprises H12MDI.

21. The polymer composition of claim 4, wherein the bloom-promoting silicone or fluorocarbon-based monomer comprises 3,3,4,4,5,5,6,6,7,7,8,8,8-tridecafluoro-1-octanol.

22. The polymer composition of claim 4, wherein the biocidally active monomer comprises 1,6-bis(biguanidinoethanol)hexane or p-chlorophenylguanidinoethanol.

23. The polymer composition of claim 4, wherein the active hydrogen compound comprises an alcohol, a diol, an amine, a diamine, a thiol, a dithiol, and combinations thereof.

24. The polymer composition of claim 1, wherein the base polymer comprises a nylon, thermoplastic polyurethane, a polyethylene, a polyester, a polyvinylchloride, a polysulfone, a polysiloxane, a polypropylene, a polycarbonate, a polyether sulfone, a polyether ether ketone, a polylactide (PLA) polymer, a poly-lactide-co-glycolide (PLG) polymer, a polycaprolactone polymer, a polydioxanol polymer, a poly(1,3-trimethylene carbonate) polymer, a polytyrosine carbonate polymer, a polyacrylate, a polymethacrylate, polylactic acid, or polyglycolic acid, and combinations thereof.

25. The polymer composition of claim 1, wherein the base polymer is a film-forming polymer.

26. The polymer composition of claim 3, wherein the bloom-promoting silicone or fluorocarbon-based monomer is present in an amount of from 5 wt % to 60 wt % of the total monomer composition of the additive.

27. The polymer composition of claim 3, wherein the biocidally active monomer is present in an amount from 0.5 wt % to about 50 wt % of the total monomer composition of the additive.

28. The polymer composition of claim 3, wherein the adhesion-promoting monomer is present in an amount of from 10 wt % to 70 wt % of the total monomer composition of the additive.

29. The polymer composition of claim 1, wherein the oligomeric or polymeric additive is present in an amount from 0.1 wt % to 20 wt % of the total polymer composition.

30. An article containing the anti-microbial polymer composition of claim 1.

31. An article including the biocidally active polymer composition of claim 1.

32. The article of claim 31, wherein the biocidally active polymer composition is coated onto a material forming the article.

33. The article of claim 32, wherein the polymer composition is coated utilizing dip coating, roll to roll coating, spin coating or spray coating.

34. The article of claim 32, wherein the biocidally active polymer composition is printed onto the material forming the article.

35. The article of claim 34, wherein the polymer composition is printed utilizing one or more of additive manufacturing or digital printing.

36. The article of claim 32, wherein the material comprises one or more of a polymer, a glass, a metal, a ceramic or a composite.

37. The article of claim 31, wherein the article is a medical device.

38. The article of claim 37, wherein the medical device comprises one or more of an angiography catheter, an angioplasty catheter, a urology catheter, a dialysis catheter, a Swan-Ganz catheter, a central venous catheter, a peripherally inserted central catheter, a catheter connector, a dialysis membrane, medical tubing, a wound care article, an orthopedic article, a neural implant, a film, a drape, a biosensor, a dental implant, a heart valve, a heart by-pass machine, an extracorporeal blood device, a nerve conduit, a vascular graft, a stent, an implant or a contact lens.

39. The article of claim 38, wherein the wound care article comprises one or more of a wound closure, a staple, a suture, a mesh, a buttressing device, a suture reinforcement, or a wound care dressing.

40. The article of claim 38, wherein the orthopedic article comprises one or more of a nail, a screw, a plate, a cage, or a prosthetic.

41. The article of claim 38, wherein the neural implant comprises one or more of a drain or a shunt.

42. The article of claim 31, wherein the article is a personal care article, a pharmaceutical article, a health care product article, or a marine article.

43. The article of claim 38, wherein the implant comprise one or more of an occular implant, a cochlear implant, or a breast implant.

44. A method of making the biocidally active polymer composition of claim 3, comprising:
   (a) free-radically polymerizing appropriate monomers to form the oligomeric or polymeric additive; and
   (b) incorporating the additive into the base polymer.

45. A method of making the biocidally active polymer composition of claim 4, comprising:
   (a) reacting the polyisocyanate and active-hydrogen monomers to form the oligomeric or polymeric additive; and
   (b) incorporating the additive into the base polymer.

46. The method of claim 44, wherein incorporating the polymeric or oligomeric additive comprises melt mixing of the additive into the base polymer or addition of the additive during synthesis of the base polymer.

47. The method of claim 44, comprising: dissolving the additive and base polymer in a common solvent and casting, coagulating, or electrospinning the solvent mixture containing the additive and the base polymer.

48. The method of claim 44, further comprising annealing the polymer composition or an article formed therefrom.

49. The method of claim 48, wherein the annealing is performed at a temperature from about the glass transition temperature of the base polymer up to the melting point of the base polymer.

50. The method of claim 49, wherein the annealing is performed at a temperature of from about 50° C. to about 150° C. for a period of from 2 hours to about 7 days.

* * * * *